(12) United States Patent
Park et al.

(10) Patent No.: US 7,662,943 B2
(45) Date of Patent: Feb. 16, 2010

(54) **PROMOTER SEQUENCES FROM *CORYNEBACTERIUM AMMONIAGENES***

(75) Inventors: Young-Hoon Park, Seongnam (KR); Hyun-Soo Kim, Anyang (KR); Hye-Jin Choi, Seoul (KR); Jin-Ho Lee, Yongin (KR); Soo-Youn Hwang, Yongin (KR); Jae-Ick Sim, Icheon (KR); Tae-Sun Kang, Seoul (KR); Won-Sik Lee, Chungju (KR)

(73) Assignee: CJ Cheiljedang Corporation, Seoul (KR)

( * ) Notice: Subject to any disclaimer, the term of this patent is extended or adjusted under 35 U.S.C. 154(b) by 400 days.

(21) Appl. No.: 11/721,515

(22) PCT Filed: Dec. 16, 2005

(86) PCT No.: PCT/KR2005/004338

§ 371 (c)(1),
(2), (4) Date: Jun. 12, 2007

(87) PCT Pub. No.: WO2006/065095

PCT Pub. Date: Jun. 22, 2006

(65) Prior Publication Data

US 2008/0138859 A1 Jun. 12, 2008

(30) Foreign Application Priority Data

Dec. 16, 2004 (KR) ...................... 10-2004-0107215

(51) Int. Cl.
*C12N 15/11* (2006.01)
*C12N 15/63* (2006.01)
*C12N 15/70* (2006.01)
*C12N 1/20* (2006.01)

(52) U.S. Cl. .................... 536/23.1; 435/320.1; 435/471

(58) Field of Classification Search ........................ None
See application file for complete search history.

(56) References Cited

U.S. PATENT DOCUMENTS 5,593,781 A 1/1997 Nass et al.
5,693,781 A 12/1997 Zupancic et al.

FOREIGN PATENT DOCUMENTS

JP 10-108675 A 4/1998
KR 1995-0000884 A 1/1995

OTHER PUBLICATIONS

Paik Jae Eun et al., "Isolation of transcription initiation signals from *Corynebacterium ammoniagenes* and comparison of their gene expression levels in *C. ammoniagenes* and *Escherichiacoli*," Biotechnology Letters, Aug. 1, 2003 vol. 25, No. 16, pp. 1311-1316, XP002351199.

Choi et al, Nov. 27, 2007, "*Corynebacterium ammoniagenes* strain ATCC 6872 heat shock protein (hsp60) gene, partial cds." Database EMBL [Online] Nov 27, 2007, 1 page, XP-002506227.

Choi et al, Nov. 27, 2007, "*Corynebacterium ammoniagenes* strain ATCC 6872 transcriptional regulator and 5-carboxymethyl-hydroxymuconate semialdehyde dehydrogenase genes, partial cds." Database EMBL [Online] Nov 27, 2007, 1 page, XP-002506228.

Choi et al, "*Corynebacterium ammoniagenes* strain ATCC 6872 5-carboxymethyl-hydroxymuconate semialdehyde dehydrogenase and homoprotocatechulate 2,3-dioxygenase genes, partial cds." Database EMBL [Online] Nov. 27, 2007, 2 pages, XP-002506229.

Choi et al, "*Corynebacterium ammoniagenes* strain ATCC 6872 putative translation elongation factor gene, partial cds." Database EMBL [Online] Nov. 27, 2007, 1 page, XP-002506230.

Choi et al, "*Corynebacterium ammoniagenes* strain ATCC 6872 putative transcriptional regulator and glyceral dehyde-3-phosphate dehydrogenase genes, partial cds." Database EMBL [Online] Nov. 27, 2007, 1 page, XP-002506231.

Choi et al, "*Corynebacterium ammoniagenes* strain ATCC 6872 putative transcriptional regulator and cysteine synthase genes, partial cds." Database EMBL [Online] Nov. 27, 2007, 1 page, XP-002506232.

Choi et al, "*Corynebacterium ammoniagenes* strain ATCC 6872 peptide methionine sulfoxide reductase A and manganese superoxide dismutase genes, partial cds." Database EMBL [Online] Nov. 27, 2007, 2 pages, XP-002506233.

Eikmanns et al. "A family of *Corynebacterium glutamicum/Escherichia coli* shuttle vectors for cloning, controlled gene expression, and promoter probing" Gene 1991, p. 93-98, V. 102.

Gory et al. "Use of green fluorescent protein to monitor *Lactobacillus sakei* in fermented meat products" FEMS Microbiology Letters, 2001, p. 127-133, V. 194.

Koizumi et al. "Production of riboflavin by metabolically engineered *Corynebacterium ammoniagenes*" Appl Microbiol Biotechnol, 2000, p. 674-679, V. 53.

Paik et al. "Isolation of transcription initiation signals from *Corynebacterium ammoniagenes* and comparison of their gene expression levels in *C. ammoniagenes* and *Escherichia coli*" Biotechnology Letters, 2003, p. 1311-1316, V. 25.

Patek et al. "Promoters from *Corynebacterium glutamicum*: cloning, molecular analysis and search for a consensus motif" Microbiology, 1996, p. 1297-1309, V. 142.

Shevchenko et al. "Mass Spectrometric Sequencing of Proteins from Silver-Stained Polyacrylamide Gels" Anal. Chem., 1996, p. 850-858, V. 68.

Van Der Rest et al. "A heat shock following electroporation induces highly efficient transformation of *Corynebacterium glutamicum* with xenogeneic plasmid DNA" Appl. Microbiol. Biotechnol., 1999, p. 541-545, V. 52.

Timko et al. "Construction of promoter-probe shuttle vectors for *Escherichia coli* and corynebacteria on the basis of promoterless alpha-amylase gene" Folia Microbiology, 2000, p. 114-120, V. 45, No. 2.

Vasicova et al. "Analysis of the *Corynebacterium glutamicum* dapA Promoter" 1999, p. 6188-6191, V. 181, No. 19.

*Primary Examiner*—Michele K. Joike
(74) *Attorney, Agent, or Firm*—Rothwell, Figg, Ernst & Manbeck, PC

(57) ABSTRACT

Provided are a promoter including at least one polynucleotide selected from the group consisting of SEQ ID NOS: 1 to 7, an expression cassette including the same, a vector including the expression cassette, a host cell including the vector, and a method of expressing a gene using the host cell.

6 Claims, 3 Drawing Sheets

PROMOTER SEQUENCES FROM *CORYNEBACTERIUM AMMONIAGENES*

CROSS REFERENCE TO RELATED APPLICATION

This application is a 35 U.S.C. § 371 National Phase Entry Application from PCT/KR2005/004338, filed Dec. 16, 2005, and designated the United States.

TECHNICAL FIELD

The present invention relates to a novel promoter nucleic acid derived from *Corynebacterium* genus bacteria, an expression cassette including the same, a vector including the expression cassette, a host cell including the vector, and a method of expressing a gene using the host cell.

BACKGROUND ART

Coryneform bacteria are microorganisms used to produce various chemical materials used in many applications, such as animal feed, medicines, and food including L-lysine, L-threonine, and various nucleic acids. A strain of coryneform bacteria showing high productivity can be developed through genetic engineering and metabolic engineering. To obtain such a strain of coryneform bacteria showing high productivity, a gene relating to various metabolic pathways needs to be expressed in the coryneform bacteria. To this end, a suitable promoter must be developed.

Generally, in coryneform bacteria, a gene is expressed under a promoter inherently included therein. (see, for example, Journal of Bacteriology, 181(19), 6188-6191, 1999). Meanwhile, the structure of a promoter sequence for expressing a gene in coryneform bacteria is not known, whereas the structures of other industrial microorganisms, such as *E. coli* and *Bacillus subtilis*, are known. Therefore, the following method has been suggested to produce promoters enabling the expression of a gene in coryneform bacteria. First, a promoter region of a gene that is resistant to an antibiotic, such as chloramphenicol, is removed. Separately, a chromosomal DNA separated from coryneform bacteria is cleaved using a suitable restriction enzyme, and the resulting fragment is introduced to the gene from which the promoter region is removed. Then, the obtained gene is used to transform coryneform bacteria to produce a transformed strain and the antibiotic resistance of the transformed strain is measured: (see Gene, 102, 93-98, 1991; Microbiology, 142, 1297-1309, 1996.) In particular, a very small number of promoters used in *Corynebacterium ammoniagenesis*, a known nucleic acid producing microorganism, has been developed. For example, a promoter having about 10% higher activity than a tac promoter is used in *E. coli* (see Biotechnol. Lett. 25, 1311-1316, 2003.) However, when it is used in a mass expression of genes, such a promoter exhibits low efficiency. U.S. Pat. No. 5,593,781 discloses a promoter DNA which is separated from a *Brevibacterium flavum* strain MJ-233 (FERM BP-1497) and has higher activity than a tac promoter. However, such a promoter DNA that is separated from a *Brevibacterium* genus may not be operable in other bacteria. Therefore, there is a need to develop a promoter sequence that is derived from commercially available *Corynebacterium ammoniagenes*, and has high activity in other bacteria.

Accordingly, the inventors of the present invention searched for a strong promoter sequence in *Corynebacterium ammoniagenes* and found that a promoter according to the present invention can express genes with high activity in *Corynebacterium ammoniagenes*.

DETAILED DESCRIPTION OF THE INVENTION

Technical Problem

Figure 1:
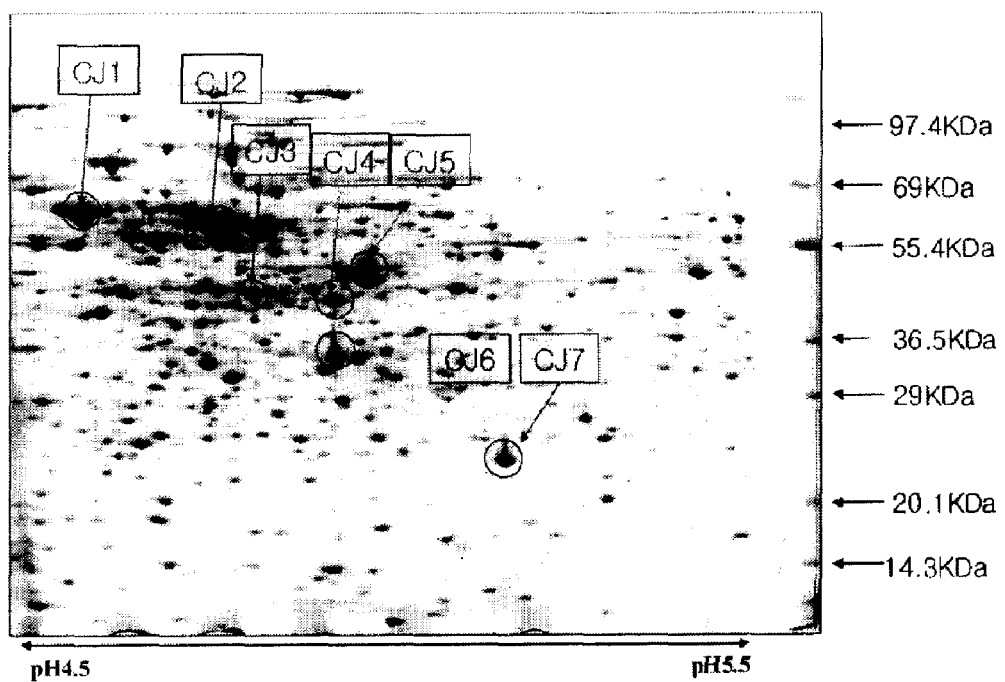
FIG. 1 shows results of two dimensional electrophoresis assay of a sample extracted from a *Corynebacterium ammoniagenes* bacterium, wherein the assay results were silver dyed and developed for identification.

The present invention provides a promoter having high activity in *Corynebacterium*.

The present invention also provides an expression cassette including the promoter and a vector including the expression cassette.

The present invention also provides a host cell including the vector.

The present invention also provides a method of expressing a gene using the host cell.

Technical Solution

The present invention provides a promoter comprising at least one polynucleotide selected from the group consisting of SEQ ID NOS: 1 through 7.

The promoter according to an embodiment of the present invention is an isolated nucleic acid and has promoter activity. Herein, the term "promoter" refers to a DNA region to which a RNA polymerase is bound to initiate transcription of a gene. The term "tac promoter" refers to a promoter obtained by fusing a sequence obtained from the —35 region of a tryptophan operon promoter of *E. coli* and a sequence obtained from the —10 region of a lactose operon promoter of *E. coli*. The tac promoter is known to have high promoter activity. A promoter having at least one nucleic acid selected from SEQ ID NOS: 1, 4, 5, 6 and 7 has higher activity in *Corynebacterium* genus bacteria than the tac promoter. In particular, a promoter having at least one nucleic acid selected from SEQ ID NOS: 1 and 4 has 10 times higher activity than the tac promoter in *Corynebacterium* genus bacteria.

The promoter according to an embodiment of the present invention has promoter activity in *Esherichia* genus bacteria, in addition to *Corynebacterium* genus bacteria. In particular, the promoter containing SEQ ID NO. 1 exhibits twice higher promoter activity than the tac promoter even in *Esherichia* genus bacteria.

The cell in which the promoter of the present invention may function can be any *Corynebacterium* genus bacteria. Examples of the *Corynebacterium* genus bacteria include *Corynebacterium ammoniagenes* CJHB100 (KCCM-10330) and ATCC 6871, *Corynebacterium glutamicum* ATCC 13032 and ATCC 13060, and the like. However, the *Corynebacterium* genus bacteria are not limited thereto. Examples of *Esherichia* genus bacteria in which a promoter according to an embodiment of the present invention may function, include *E. coli*.

The sequence of the promoter according to an embodiment of the present invention can be easily changed by a person having ordinary skill in the art through a known mutagenesis process, such as directed evolution and site directed mutagenesis. Accordingly, a nucleic acid that has, for example, 70% or more homology, preferably 80% or more homology, and more preferably, 90% or more homology, with the isolated promoter sequence including at least one nucleic acid selected from SEQ ID NOS: 1 to 7, and can act as a promoter in *Corynebacterium* genus bacteria is included in the scope of the present invention.

The present invention also provides an expression cassette including the promoter which is operably linked to a coding sequence. The coding sequence may be, for example, the entire gene or a coding sequence which codes a predetermined region of the gene. Herein, the term "operably linked" indicates that the coding sequence is functionally connected to the promoter such that the promoter sequence can initiate or mediate transcription of the coding sequence. The cassette according to an embodiment of the present invention may further include 5' and 3' control sequences operably linked to the promoter sequence. The coding sequence may be a gene associated with a metabolic product, such as IMP, GMP, L-lysine and L-threonine.

The present invention also provides a vector including the expression cassette according to an embodiment of the present invention. Herein, the vector is not limited, and can be any vector known in the art. Examples of the vector according to embodiments of the present invention include a pCR2.1-TOPO vector (produced from Invitrogen Inc, USA) and pECCG117 (KFCC-10673). However, the vector is not limited thereto. Examples of the vector including the expression cassette according to an embodiment of the present invention include p117-cj1-gfp, p117-cj2-gfp, p117-cj3-gfp, p117-cj4-gfp, p117-cj5-gfp, p117-cj6-gfp and p117-cj7-gfp.

The present invention also provides a host cell including the vector according to an embodiment of the present invention. The host cell may be a *Corynebacterium* genus bacteria or an *Esherichia* genus bacteria, but is not limited thereto. For example, the host cell may be *Corynebacterium ammoniagenes* CJHB100 (KCCM-10330) or *E. coli*.

The present invention also provides a method of expressing an exogenous gene by culturing the host cell. The host cell is cultured in one of various known culture mediums and under various known culture conditions according to the selected host cell.

Advantageous Effects

A gene that is operably linked to a promoter according to the present invention is efficiently expressed in *E. coli* and *Corynebacterium ammoniagenes*. The promoter is suitable for developing a strain using *Corynebacterium* genus bacteria.

An expression cassette including the promoter according to the present invention and a vector including the expression cassette according to the present invention are suitable for efficiently expressing an exogenous gene in *E. coli* and *Corynebacterium ammoniagenes*.

A host cell according to the present invention can efficiently express an exogenous gene.

By using a method of expressing a gene according to the present invention, an exogenous gene can be efficiently expressed.

Best Mode

The present invention will be described in further detail with reference to the following examples. These examples are for illustrative purposes only, and are not intended to limit the scope of the present invention.

EXAMPLES

Bacterial extracts were prepared from *Corynebacterium ammoniagenes* CJHB100 (KCCM-10330) at various cultural stages. Two-dimensional electrophoresis was performed on the bacterial extracts to find overexpressed proteins therein, which were then cleaved to analyze peptide sequences. The obtained peptide sequences were used to identify genes of the overexpressed proteins. Then, promoter regions were isolated, and vectors were produced using the promoter regions. Next, the activities of the promoter in *Corynebacterium ammoniagenes* CJHB100 (KCCM-10330) and *E. coli* were measured.

Example 1

Culturing of *Corynebacterium Ammoniagenes* CJHB100 (KCCM-10330) and Selection of Overexpresssion Protein According to Cultural Stages (1) Culturing of Bacteria

*Corynebacterium ammoniagenes* CJHB100 (KCCM-10330) were cultured in a medium having raw sugar of molasses (mixture containing 50% glucose and 50% fructose), At this time, the cell concentration was measured. Samples of the cultured *Corynebacterium ammoniagenes* CJHB100 (KCCM-10330) were harvested at an early stationary phase and stationary phases. The samples were centrifuged and the resulting upper solution was removed. The obtained cell pellet was lysed in a disintegrating buffer to produce about 100 μm of a bacterial extract.

(2) Two-dimensional Electrophoresis Assay

The bacterial extract obtained from section (1) was diluted using 6M urea, 2M thiourea, 4% CHAPS, and 0.4% DTT to obtain a mixture with a total volume of 350 μl. Then, 7 μl of an IPG buffer and 3 μl of 1% bromophenol blue (BPB) were added thereto. The resulting solution was loaded onto a rehydration tray using an immobiline pH gradient drystrip. The sample on the rehydration tray was covered with 2 ml of a cover liquid to prevent vaporization of the sample and crystallization of the urea, and then rehydrated at room temperature for about 24 hours.

The rehydrated strip gel was subjected to isoelectric focusing at 20° C. at 0-100 V for 1 hour, at 300 V for 1 hour, at 600 V for 1 hour, and at 8000 V for a predetermined time, which was adjusted to perform focusing for 43-97 kVhr (pH 4-7: 43.4 kVhr, pH 4.5-5.5, pH 5.5-6.7:97 kVhr) using an isoelectric focusing device (Multiphor II: produced by Amersham Bioscience, USA.).

When isoelectric focusing was completed, respective strip gels were equilibrated in a pH 8.8 solution containing 20 mM Tris-HCl, 6M urea, 2% SDS, 20% glycerol, 2.5% acrylamide and 5 mM TBP for 15 minutes. Respective equilibrated strips was loaded onto a two-dimensional gel (9-16% concentration gradient)) and then sealed with an SDS solution containing 0.5% agarose having a low boiling point and 0.001% BPB. The electrophoresis was performed at 100 V for about 19 hours.

After the electrophoresis was completed, the gel was immobilized in a 45% methanol solution and 5% acetic acid solution. The acetic acid was washed for 1 hour using distilled water. The gel was sensitized with 0.02% sodium thiosulfate for 2 minutes and washed with distilled water. Then, the gel was reacted with 0.1% silver nitrate for 20 minutes and washed with distilled water. The reaction product was developed with a solution containing 2% (w/v) sodium carbonate and 0.04% (v/v) formaldehyde. When a spot having desired strength appeared, the reaction was stopped using 1% acetic acid. The gel was washed with distilled water and stored in a sealed plastic bag at 4° C.

When coomassie staining is used, after the electrophoresis was completed, the gel was fixed using a 30% methanol solution and a 10% acetic acid solution for 1 hour, washed with distilled water, stained with colloidal coomassie brilliant G-250 for 24 hours, and then bleached with a 10% methanol solution and a 7% acetic acid solution for 4 hours.

(3) Preparing of Peptide Sample Used for Mass Spectrometry Based on Spots

Peptide was separated from spots using a modified version of a known method (Shevchenko et al. Anal. Chem., 68(5), 850-8, 1996.) First, a protein spot was cleaved from the gel prepared in Section (2), bleached in 120 μl of a mixed solution of 30 mM potassium ferricyanide and 100 mM of sodium thiosulfate at a ratio of 1:1, and washed with distilled water and then with 120 μl of 50% acetonitrile/25 mM ammonium bicarbonate (pH 7.8) for 10 minutes. The resultant product was reacted with 50 μl of 100% acetonitrile until a white color had appeared for about 5 minutes and then vacuum dried.

10 μl of two dimensional electrophoresis grade trypsin (0.02 μg/μl) was added to the dried spots and then reacted in ice for 45 minutes. Then, 50 mM of an ammonium bicarbonate buffer (pH 7.8) was added to the reaction product and reacted at 37° C. for 12-14 hours. The resultant product was treated three times with ultrasonic waves for 10 minutes in 10 μl of 0.5% TFA and 50% acetonitrile to extract a peptide.

(4) Mass Spectrometry

The peptide extracted as described above was assayed through HPLC-MS/MS. The HPLC-MS/MS was performed with 1100 series HPLC system (produced from Agilient Inc, USA) and a Finnigan LCQ DECA ion-trap mass spectrometery device (produced from ThermoQuest, USA) on which a nano spray ionized source was installed. The HPLC was performed with a C18 microprobe reversed phase column, 0.1% formic acid (solvent A) and solution (solvent B) of 90% (v/v) acetonitrile and 0.1% formic acid was provided in a linear grade (flow rate=1 μl/min) to isolate a peptide.

The peptide detection was performed 3 times using nano spray ionization (NSI) (spray voltage: 1.8 kV; capillary temperature: 200° C.; capillary voltage: 34 V; pipe lens offset: 40 V; and electron multiplier: −60 V). The measurements were obtained in a centroid mode. After the entire MS scan of 400-2000 Da was obtained, a threshold value was set to $1 \times 10^5$ counts and the strongest ions were separated through a high resolution zoom scan. Then, collision-induced dissociation (CID) MS/MS was performed. The sequence of a CID spectrum that was not encoded was identified using TurboQuest software (produced by Thermo Finnigan Inc, USA). The results of a SEQUEST search were identified through cross-correlation and ΔCn (delta normalized correlation).

The sequence of an amino acid of the peptide was confirmed and identified using Q-star Pulsar LC MS/MS (produced by Applied Biosystems Inc, USA).

As a result, 50 proteins were found, and seven overexpressed proteins of the 50 proteins were selected. FIG. 1 shows results of two dimensional electrophoresis assay of a sample extracted from a *Corynebacterium ammoniagenes*, in which the assay results were silver stained and developed for identification. In FIG. 1, seven overexpressed spots denoted by CJ1 through CJ7 were identified. The functions of these seven overexpressed proteins were indicated in Table 1. The functions of these proteins were identified by comparing the sequence of the peptide to an amino acid sequence contained in the NCBI gene bank database.

TABLE 1

| Spot Name | Protein | Gene bank accession No. |
|---|---|---|
| | Heat shock protein hsp60 | AE008903.1 |
| | 5-carboxy methyl-2-hydroxy muconate semialdehyde dehydrogenase | NC-006461.1 |
| | Homoprotocateculate 2,3-dioxygenase | NC-005835.1 |
| | Temporary translation extension factor EF-Tu | YP-145957 |
| | Glyceraldehyde-3-phosphate dehydrogenase | AAA69094 |
| | Cysteine synthase | AAV89445 |
| | Manganese superoxide dismutase | NP-940564 |

A gene sequence was assumed from the seven overexpressed proteins and analyzed to select a promoter region. As a result, it was assumed that oligonucleotides of SEQ. ID NOS: 1 through 7 separated from the gene sequence corresponding to the proteins denoted by CJ1 to CJ7 have promoter activity.

Example 2

Manufacturing of Recombinant Vector p117-cj1~7-gfp Having Promoter Sequence and Confirming of Promoter Activity in *Corynebacterium Ammoniagenes*

(1) Amplifying of Promoter Sequence from Genome of *Corynebacterium ammoniagenes* CJHB100

500 μg of chromosomal DNA was separated from 25 ml of *Corynebacterium ammoniagenes* CJHB100 culture incubated for one day, using a method suggested by Eikmann et al. (Gene, 102, 93-98, 1991). The separated chromosomal DNA was used as a template. PCRs were performed using primer sets (SEQ ID NOS: 10 and 11, 12 and 13, 14 and 15, 16 and 17, 18 and 19, 20 and 21, and 22 and 23) to amplify promoters of CJ1 to CJ7 for 30 seconds at 94° C., at 55° C., and at 72° C., repeated 30 times, respectively. As a result, respective promoter sequences pcj1 through pcj7 were amplified.

(2) Manufacturing of Screening Vector

Figure 2:
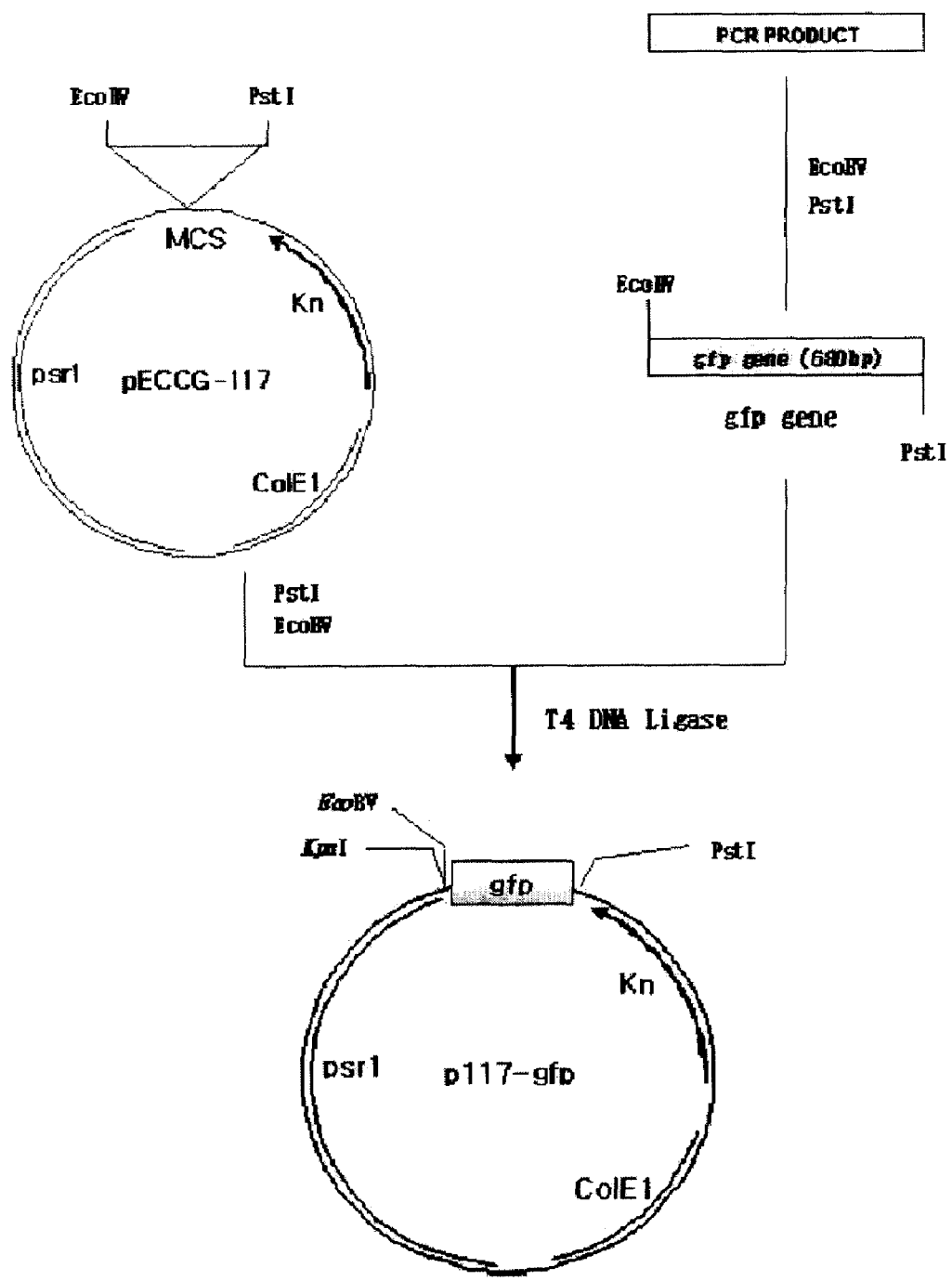
FIG. 2 illustrates a method of producing a screening vector of p117-gfp according to an embodiment of the present invention.

First, PCRs were performed using a pGFuv vector (produced by Clontech Inc, USA) as a template and using SEQ ID NOS: 8 and 9 as a primer at 94° C. for 30 seconds, at 55° C. for 30 seconds, and at 72° C. for one minute, respectively. The PCR was performed 30 times at each temperature. As a result, a green fluorescent protein (GFP) gene that did not include a promoter region was amplified. Then, the obtained GFP gene that did not include a promoter region was cloned into pCR2.1-TOPO vectors (produced from Invitrogen, USA), which were then cleaved by PstI and EcoRI and introduced to PstI and EcoRI site of pECCG117 (KFCC-10673/KFCC-10674), which is a shuttle vector and can be expressed in *E. coli* and coryneform bacteria. The result was used as a screening vector (p117-gfp) to separate the promoter. FIG. 2 illustrates a method of producing the screening vector of p117-gfp according to an embodiment of the present invention (3) Introducing of Promoter Sequence to Screening Vector and Identifying of Promoter Activity in *Corynebacterium ammoniagenes* CJHB100

Figure 3:
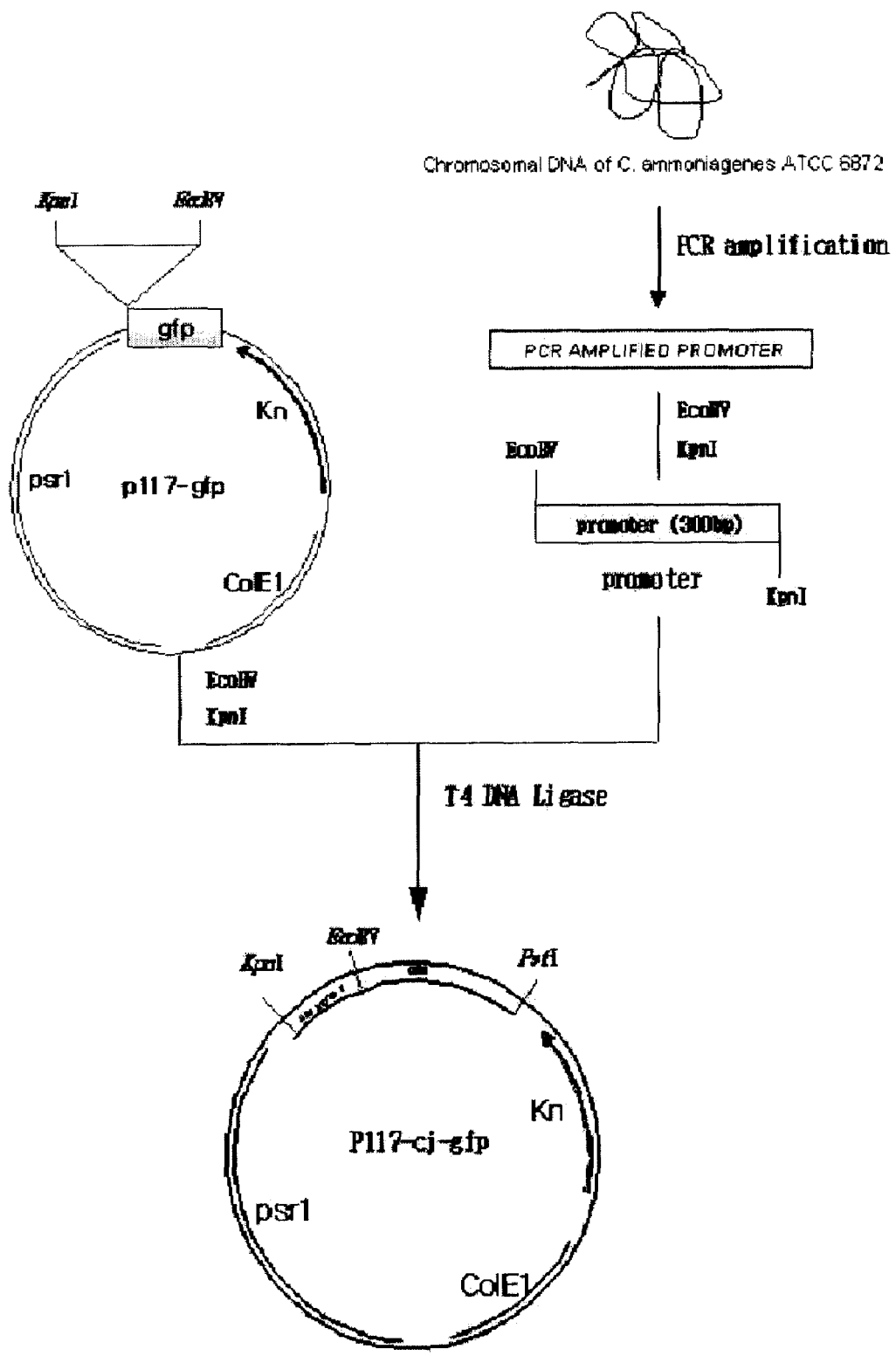
FIG. 3 illustrates a method of producing a recombinant vector including promoter sequence pcj1 through pcj7 from a screening vector p117-gfp according to an embodiment of the present invention.

The screening vector obtained in Section (2) was cleaved with a restriction enzyme of KpnI/EcoRV and then ligated to the promoter sequences of pcj1 through pcj7 that had been cleaved by the same restriction enzyme to produce recombinant vectors of p117-cj1-7-gfp in which oligonucleotides of pcj1 through pcj7, which were separated from *Corynebacterium ammoniagenes* CJHB100 and had assumed promoter activity, were ligated to the GFP. FIG. 3 illustrates a method of producing a recombinant vector including SEQ. ID NOS: pcj1 through pcj7 from the screening vector p117-gfp according to an embodiment of the present invention.

The obtained recombinant vector was introduced to *Corynebacterium ammoniagenes* CJHB100 (KCCM-10330) ready for transformation through a method introduced by van der Rest et al. (Appl. Microbiol. Biotechnol., 52, 541-545, 1999). The resultant transformed strain was smeared onto a CM medium (1% peptone, 1% broth, 0.25% sodium chloride, 1% yeast extract, 100 mg/ml adenine, 100 mg/ml guanine, 2% agar (pH 7.2)) containing 10 µg/ml of kanamycin and cultured at 32° C. for 3 days. A viable strain showing a growth was screened from the colonies. Then, ultraviolet light was radiated onto the screened strain and strains radiating a fluorescence was selected.

Screening of the strains radiating a fluorescence indicates that promoters of pcj1 through pcj7 exhibit promoter activity in a coryneform bacterium.

Meanwhile, promoter activity was quantitatively measured. The recombinant vector of p117-cj1-7-gfp was introduced into *Corynebacterium ammoniagenes* CJHB100 (KCCM-10330) and cultured in the same manner as described above. The culture was centrifuged to obtain bacteria pellet. Then, bacterial pellet was suspended in a protein extract buffer (EDTA 1 mM of PBS, 3% glycerol, 1% triton-X-100 solution, pH-7.5) and was lysed by ultrasonication. The lysate was centrifuged and the resulting upper solution containing a bacterial extract was separated. The amount of the protein contained in the bacterial extract was measured through a Bradford assay method. Subsequently, 488 nm light was radiated onto a bacterial extract equal in amount to the bacterial extract described above using a method introduced by Laure Gory et al. (FEMS Microbiology Letters 194,127-133, 2001) and emitted light was measured using a LS-50B spectrophotometer (Perkin-Elmer) to find a degree of expression of the GFP gene and found to have a wavelength of 511 nm.

The results are shown in Table 2. As shown in Table 2, the promoter according to an embodiment of the present invention directs an efficient expression of a GFP gene. More particularly, promoters of pcj1 and pcj4 exhibited the highest efficiency compared to the other promoters.

TABLE 2

| Promoter | pcj1 | pcj2 | pcj3 | pcj4 | pcj5 | pcj6 | pcj7 |
|---|---|---|---|---|---|---|---|
| | 12309 | 437 | 479 | 11790 | 1363 | 5651 | 2493 |

Example 3

Comparison of Activities of Tac Promoter and Promoter According to an Embodiment of the Present Invention in *Corynebacterium Ammoniaqenes*

In the present experiment, the activities of a promoter according to an embodiment of the present invention and a tac promoter that is conventionally used in *Corynebacterium ammoniagenes* were compared.

(1) Manufacturing of Vector Containing Sequence of tac Promoter and GFP Gene Combined First, a PCR was performed using a pKK223-2 vector (produced by Pharmacia Biotech, USA) as a template and using SEQ ID NOS: 24 and 25 as a primer in the same manner as in Example 1 to amplify the tac promoter sequence. The amplified product was cloned into a pCR2.1-TOPO vector (Invitrogen, USA). Next, the obtained tac promoter sequence was cleaved with restriction enzymes of KpnI and EcoRV and ligated to p117-gfp that had been cleaved with the same restriction enzymes to obtain a recombinant expression vector (p117-tac-gfp.)

The recombinant vector was used to transform *Corynebacterium ammoniagenes* CJHB100 in the same manner as in Example 1, and the activity of a GFP gene was measured. The activity of the GFP gene due to the tac promoter was compared to the activity of the GFP gene due to the promoter selected according to Example 2. The results are shown in Table 3.

TABLE 3

| Promoter | pcj1 | pcj2 | pcj3 | pcj4 | pcj5 | pcj6 | pcj7 | Ptac |
|---|---|---|---|---|---|---|---|---|
| | 1140% | 40% | 44% | 1092% | 126% | 523% | 231% | 100% |

As shown in Table 3, it was found that a promoter according to an embodiment of the present invention efficiently expressed a GFP gene. In addition, when the activity of promoters according to an embodiment of the present invention in *Corynebacterium ammoniagenes* is compared to the activity of the tac promoter in *Corynebacterium ammoniagenes*, the pcj1, pcj4, pcj5, pcj6 and pcj7 promoters exhibited higher intensities than the tac promoter. In particular, promoters of pcj1 and pcj4 exhibited 10 times the activity of the tac promoter.

Example 4

Confirmation of Activity of Promoter According to the Present Invention in *E. coli*

It was confirmed that the promoter according to an embodiment of the present invention exhibited activity in *E. coli* in addition to coryneform bacteria. *E. coli* was transformed with the recombinant expression vector used in Examples 1 and 2.

It was determined whether the promoter according to an embodiment of the present invention enables efficient expression of the GFP gene in *E. coli* by measuring the activity of the GFP gene in the same manner as in Example 1. A reference vector was a tac promoter-containing a recombinant vector of p117-tac-gfp. Table 4 shows promoter activity of promoters according to embodiments of the present invention in *E. coli*.

TABLE 4

| Promoter | pcj1 | pcj2 | pcj3 | pcj4 | pcj5 | pcj6 | pcj7 | ptac |
|---|---|---|---|---|---|---|---|---|
| | 296% | 15% | 20% | 17% | 19% | 24% | 24% | 100% |

As shown in Table 4, it was found that the promoter according to an embodiment of the present invention efficiently expressed the GFP gene in *E. coli*. More particularly, the pcj1 promoter exhibited high activity in both coryneform bacteria and *E. coli*.

Example 5

Effects of IPTG on Activity of Promoter According to the Present Invention

It is well known that a tac promoter is a representative promoter by which gene expression is inducible by IPTG (isopropylthio-β-D-galactoside) in *E. coli*. In other words, in *E. coli*, the amount of a gene expressed by the tac promoter varies according to the presence or absence of IPTG.

In the present experiment, the effects of IPTG on the expression of a GFP gene by a promoter according to an embodiment of the present invention were measured. To this end, a recombinant vector containing the pcj1 promoter that has higher activity than the other promoters of p117-cj1-gfp was introduced into *E. coli* and *Corynebacterium ammoniagenes* CJHB100 (KCCM-10330) in the same manner as in Examples 1 and 2, and the amount of the GFP gene expressed thereby was measured. The reference was a tac promoter-containing recombinant vector of p117-tac-gfp.

The results are shown in Table 5.

TABLE 5

| Host cell | *Corynebacterium ammoniagenes* CJHB100 | | | | *E. coli* | | |
|---|---|---|---|---|---|---|---|
| Induction | IPTG induction | | No induction | | IPTG induction | | No induction |
| Promoter | ptac | pcj1 | ptac | pcj1 | ptac | pcj1 | ptac |
| Fluorescence Intensity | 2089 | 5530 | 1959 | 5048 | 6480 | 7165 | 2314 |

As shown in Table 5, a promoter according to an embodiment of the present invention more efficiently expressed a GFP gene in *E. coli* and *Corynebacterium ammoniagenes* than a tac promoter, regardless of the presence of IPTG.

Promoters of pCJ1, pCJ2, pCJ3, pCJ4, pCJ5, pCJ6 and pCJ7 obtained in the Examples described above were inserted into pECCG117. The obtained vectors were used to transform *E. coli* DH5. The resultant transformants were deposited in Korean Cuture Center of Microorganisms (KCCM), which is an international deposition organization under the Bupest Treaty, on 11 Jun. 2004 (deposition numbers: KCCM-10611, KCCM-10612, KCCM-10613, KCCM-10614, KCCM-10615, KCCM-10616, and KCCM-10617).

The invention claimed is:

1. An isolated promoter comprising at least one polynucleotide selected from the group consisting of SEQ ID NOS: 1 through 7.

2. An expression cassette, which comprises the promoter of claim 1 and is operably linked to a coding sequence.

3. A vector comprising the expression cassette of claim 2.

4. A host cell comprising the vector of claim 3.

5. The host cell of claim 4 being a bacterial cell belonging to a *Corynebacterium* genus or an *Esherichia* genus.

6. A method of expressing an exogenous gene comprising culturing the host cell of claim 4.

* * * * *

SEQUENCE LISTING

```
<160> NUMBER OF SEQ ID NOS: 24

<210> SEQ ID NO 1
<211> LENGTH: 301
<212> TYPE: DNA
<213> ORGANISM: Corynebacterium ammoniagenes CJHB100

<400> SEQUENCE: 1
caccgcgggc ttattccatt acatggaatg accaggaatg gcagggaatg cgacgaaatt     60
gactgtgtcg ggagcttctg atccgatgct gccaaccagg agagaaaata atgacatgtg    120
caggcacgct ggtgagctgg agatttatga tctcaagtac cttttttctt gcactcgagg    180
gggctgagtg ccagaatggt tgctgacacc aggttgaggt tggtacacac tcaccaatcc    240
tgccgtcgcg ggcgcctgcg tggaacataa accttgagtg aaacccaatc taggagatta    300
a                                                                    301

<210> SEQ ID NO 2
<211> LENGTH: 285
<212> TYPE: DNA
<213> ORGANISM: Corynebacterium ammoniagenes CJHB100

<400> SEQUENCE: 2
aattccacca gacgttgttt agtaagtgcc cgaattctcg gttggtgcag ttgcttttcg     60
atgaatggga gaacctcgaa tacttccgcg tctctacttt ccggtacgtg ccacacagag    120
cagagcaatc ggtggaagag cacgacagat tagtagcgct tatcgaagcc caggcagaag    180
atttctacat cgaatcccaa gcccgcaacc accgcctgac aaccgcaacg acctaccgcc    240
aacgtttaaa ttccgaaaat catcacgaag aacaaggagt gcaca                    285
```

<210> SEQ ID NO 3
<211> LENGTH: 291
<212> TYPE: DNA
<213> ORGANISM: Corynebacterium ammoniagenes CJHB100

<400> SEQUENCE: 3

```
gctgcctaca tctggacttc tgacctgaag cgctcccaca acttcgcgca aaacgttgaa      60
gccggcatgg tctggttgaa ctccaacaac gtccgtgacc tgcgcacccc attcggtggc     120
gtcaaggcat ccggtctggg gcatgagggc ggctaccgct ccattgactt ctacaccgac     180
caacaggccg tacacatcaa cttaggcgaa gtccacaacc cagtcttcgg caagcaaacc     240
aactaattct ccctcatcca cactccccTt ttaacctcac taggagtcat c              291
```

<210> SEQ ID NO 4
<211> LENGTH: 312
<212> TYPE: DNA
<213> ORGANISM: Corynebacterium ammoniagenes CJHB100

<400> SEQUENCE: 4

```
actgggaggg taggggtcac gctgaattag caggtcacat cctgttgctt gagctggccg      60
ttaccctcct aggatccgag atgattcttg tagaggacta acgtccgcac aaatcttccg     120
cgggatgctc aaatcaccct tagctggttt gaaaaatccg tggcataaat ctaggatcgt     180
gtaactggca cgaaaagaaa gcgtcatcgg cgcttgggaa catctttttta agatattcct     240
caagtgccgt gacatctgtc aaccccgtgg ctgcagagt cgtagtcaca atgaagtcca      300
ggaggacata ca                                                         312
```

<210> SEQ ID NO 5
<211> LENGTH: 249
<212> TYPE: DNA
<213> ORGANISM: Corynebacterium ammoniagenes CJHB100

<400> SEQUENCE: 5

```
tcggacatat acggatttac ctgctgcaat cgcgccggcc cttgctcgaa attgcgtgaa      60
ttttagtctg attgtgttgg aatatccgca gaatgtgtgg gtttgctttt ataaatctgc     120
gcagtgtagg gaacctcggt actatcggca gtgtcggaga aacttcctcg atataaatct     180
ttgaagtaat tctcccaggc aatagctttt gacgtactcc gcttcccaac tttttaggag     240
acaactacc                                                             249
```

<210> SEQ ID NO 6
<211> LENGTH: 332
<212> TYPE: DNA
<213> ORGANISM: Corynebacterium ammoniagenes CJHB100

<400> SEQUENCE: 6

```
ggcttcatcg tcgtctttga tccgatgcga gtccattaac ccaaactcct taaagcccgt      60
aaaacggggg tattccaaca cggttatcca cagtttaacc gttattcggg ggtaatccta     120
acccaaatca ttacggaaac tccaatctgg ctcacaatat cctccatgat tctagggaca     180
cccaatcagg tgcacccgct tcctgcgaca acgagtcaaa ctcggcaaag ccctcaacct     240
gtcggtctag aatatatata ccgcccggtc tagtgttgtg gtgtacacta acgataaacc     300
aacaaagttg tctattaaga ggaggccatt tc                                    332
```

<210> SEQ ID NO 7

-continued

```
<211> LENGTH: 318
<212> TYPE: DNA
<213> ORGANISM: Corynebacterium ammoniagenes CJHB100

<400> SEQUENCE: 7
agaaacatcc cagcgctact aatagggagc gttgaccttc cttccacgga ccggtaatcg     60
gagtgcctaa aaccgcatgc ggcttaggct ccaagatagg ttctgcgcgg ccgggtaatg    120
catcttcttt agcaacaagt tgaggggtag gtgcaaataa gaacgacata gaaatcgtct    180
cctttctgtt tttaatcaac atacaccacc acctaaaaat tccccgacca gcaagttcac    240
agtattcggg cacaatatcg ttgccaaaat attgtttcgg aatatcatgg gatacgtacc    300
caacgaaagg aaacactc                                                  318

<210> SEQ ID NO 8
<211> LENGTH: 31
<212> TYPE: DNA
<213> ORGANISM: Artificial Sequence
<220> FEATURE:
<223> OTHER INFORMATION: primer

<400> SEQUENCE: 8
acgcgatatc atgagtaaag gagaagatct t                                    31

<210> SEQ ID NO 9
<211> LENGTH: 31
<212> TYPE: DNA
<213> ORGANISM: Artificial Sequence
<220> FEATURE:
<223> OTHER INFORMATION: primer

<400> SEQUENCE: 9
aaaactgcag ttatttgtag agctcatcca t                                    31

<210> SEQ ID NO 10
<211> LENGTH: 32
<212> TYPE: DNA
<213> ORGANISM: Artificial Sequence
<220> FEATURE:
<223> OTHER INFORMATION: primer

<400> SEQUENCE: 10
cggggtacca ccgcgggctt attccattac at                                   32

<210> SEQ ID NO 11
<211> LENGTH: 32
<212> TYPE: DNA
<213> ORGANISM: Artificial Sequence
<220> FEATURE:
<223> OTHER INFORMATION: primer

<400> SEQUENCE: 11
acgcgatatc ttaatctcct agattgggtt tc                                   32

<210> SEQ ID NO 12
<211> LENGTH: 33
<212> TYPE: DNA
<213> ORGANISM: Artificial Sequence
<220> FEATURE:
<223> OTHER INFORMATION: primer

<400> SEQUENCE: 12
cggggtacca attccaccag acgttgttta gta                                  33
```

<210> SEQ ID NO 13
<211> LENGTH: 32
<212> TYPE: DNA
<213> ORGANISM: Artificial Sequence
<220> FEATURE:
<223> OTHER INFORMATION: primer

<400> SEQUENCE: 13
acgcgatatc tgtgcactcc ttgttcttcg tg                    32

<210> SEQ ID NO 14
<211> LENGTH: 33
<212> TYPE: DNA
<213> ORGANISM: Artificial Sequence
<220> FEATURE:
<223> OTHER INFORMATION: primer

<400> SEQUENCE: 14
cggggtaccg ctgcctacat ctggacttct gac                   33

<210> SEQ ID NO 15
<211> LENGTH: 31
<212> TYPE: DNA
<213> ORGANISM: Artificial Sequence
<220> FEATURE:
<223> OTHER INFORMATION: primer

<400> SEQUENCE: 15
acgcgatatc gatgactcct agtgaggtta a                     31

<210> SEQ ID NO 16
<211> LENGTH: 29
<212> TYPE: DNA
<213> ORGANISM: Artificial Sequence
<220> FEATURE:
<223> OTHER INFORMATION: primer

<400> SEQUENCE: 16
cggggtacca ctgggagggt aggggtcac                        29

<210> SEQ ID NO 17
<211> LENGTH: 30
<212> TYPE: DNA
<213> ORGANISM: Artificial Sequence
<220> FEATURE:
<223> OTHER INFORMATION: primer

<400> SEQUENCE: 17
acgcgatatc tgtatgtcct cctggacttc                       30

<210> SEQ ID NO 18
<211> LENGTH: 32
<212> TYPE: DNA
<213> ORGANISM: Artificial Sequence
<220> FEATURE:
<223> OTHER INFORMATION: primer

<400> SEQUENCE: 18
cggggtacct cggacatata cggatttacc tg                    32

<210> SEQ ID NO 19
<211> LENGTH: 31
<212> TYPE: DNA
<213> ORGANISM: Artificial Sequence
<220> FEATURE:
<223> OTHER INFORMATION: primer

<400> SEQUENCE: 19

-continued

```
acgcgatatc gttgtctcct aaaaagttgg g                              31

<210> SEQ ID NO 20
<211> LENGTH: 25
<212> TYPE: DNA
<213> ORGANISM: Artificial Sequence
<220> FEATURE:
<223> OTHER INFORMATION: primer

<400> SEQUENCE: 20
cggggtaccg gcttcatcgt cgtct                                     25

<210> SEQ ID NO 21
<211> LENGTH: 30
<212> TYPE: DNA
<213> ORGANISM: Artificial Sequence
<220> FEATURE:
<223> OTHER INFORMATION: primer

<400> SEQUENCE: 21
acgcgatatc atggcctcct cttaatagac                                30

<210> SEQ ID NO 22
<211> LENGTH: 33
<212> TYPE: DNA
<213> ORGANISM: Artificial Sequence
<220> FEATURE:
<223> OTHER INFORMATION: primer

<400> SEQUENCE: 22
cggggtacca gaaacatccc agcgctacta ata                            33

<210> SEQ ID NO 23
<211> LENGTH: 29
<212> TYPE: DNA
<213> ORGANISM: Artificial Sequence
<220> FEATURE:
<223> OTHER INFORMATION: primer

<400> SEQUENCE: 23
acgcgatatc agtgtttcct ttcgttggg                                 29

<210> SEQ ID NO 24
<211> LENGTH: 29
<212> TYPE: DNA
<213> ORGANISM: Artificial Sequence
<220> FEATURE:
<223> OTHER INFORMATION: primer

<400> SEQUENCE: 24
cggggyaccc ggagcttatc gactgcacg                                 29
```